United States Patent
Carter

(10) Patent No.: US 12,138,448 B2
(45) Date of Patent: Nov. 12, 2024

(54) TISSUE-STIMULATING PROSTHESIS DISSOLUTION BARRIER

(71) Applicant: Cochlear Limited, Macquarie University (AU)

(72) Inventor: Paul Michael Carter, West Pennant Hills (AU)

(73) Assignee: Cochlear Limited, Macquarie University (AU)

( * ) Notice: Subject to any disclaimer, the term of this patent is extended or adjusted under 35 U.S.C. 154(b) by 693 days.

(21) Appl. No.: 17/413,712

(22) PCT Filed: Jun. 10, 2020

(86) PCT No.: PCT/IB2020/055450
§ 371 (c)(1),
(2) Date: Jun. 14, 2021

(87) PCT Pub. No.: WO2020/250148
PCT Pub. Date: Dec. 17, 2020

(65) Prior Publication Data
US 2022/0032046 A1  Feb. 3, 2022

Related U.S. Application Data

(60) Provisional application No. 62/860,946, filed on Jun. 13, 2019.

(51) Int. Cl.
*A61N 1/05* (2006.01)
*A61N 1/36* (2006.01)

(52) U.S. Cl.
CPC ....... *A61N 1/0541* (2013.01); *A61N 1/36038* (2017.08)

(58) Field of Classification Search
CPC .................. A61N 1/0541; A61N 1/36038
(Continued)

(56) References Cited

U.S. PATENT DOCUMENTS

| 6,019,877 A | 2/2000 | Dupelle et al. |
| 2006/0004432 A1 | 1/2006 | Parker et al. |

(Continued)

FOREIGN PATENT DOCUMENTS

| CN | 1583191 A | 2/2005 |
| WO | 2002089906 A2 | 11/2002 |

OTHER PUBLICATIONS

Extended European Search Report in counterpart European Application No. 20823183.7-1126, mailed May 31, 2023, 7 pages.

(Continued)

*Primary Examiner* — Nadia A Mahmood
(74) *Attorney, Agent, or Firm* — Edell, Shapiro & Finnan, LLC

(57) ABSTRACT

Presented herein are dissolution barriers for use with tissue-stimulating prostheses. As described further below, a tissue-stimulating prosthesis comprises a stimulating assembly including an elongate insulating carrier member and a plurality of electrode contacts disposed along the carrier member. A continuous dissolution barrier is disposed on the surface of the stimulating assembly so as to substantially encapsulate/enclose the plurality of electrode contacts and the carrier member. The continuous dissolution barrier is configured to inhibit in situ dissolution of the plurality of electrode contacts.

30 Claims, 8 Drawing Sheets

(58) Field of Classification Search
USPC .......................................................... 607/137
See application file for complete search history.

(56) References Cited

U.S. PATENT DOCUMENTS

| | | | |
|---|---|---|---|
| 2009/0192580 A1 | 7/2009 | Desai | |
| 2010/0331811 A1 | 12/2010 | Imran | |
| 2011/0126410 A1 | 6/2011 | Capcelea et al. | |
| 2011/0178587 A1 | 7/2011 | Chambers | |
| 2011/0257702 A1 | 10/2011 | Kara et al. | |
| 2012/0157804 A1* | 6/2012 | Rogers .................. | H01L 24/50 604/20 |
| 2018/0117310 A1 | 5/2018 | Sibary et al. | |
| 2018/0132790 A1 | 5/2018 | Yao et al. | |

OTHER PUBLICATIONS

Hassarati, R. T. et al., "Improving Cochlear Implant Properties Through Conductive Hydrogel Coatings", IEEE Transactions on Neural Systems and Rehabilitation Engineering, vol. 22, Issue: 2, Mar. 2014, pp. 411-418.

Aregueta-Robles, Ulises A. et al., "Organic electrode coatings for next-generation neural interfaces", doi: 10.3389/fneng.2014.00015, May 27, 2014, 18 pages.

Donaldson, N de N. et al., "Performance of platinum stimulating electrodes mapped on the limit-voltage plane", Part 2: Corrosion in vitro, Med. & Biol. Eng. & Comput. 1986, vol. 24, pp. 431-438.

Nadol Jr., Joseph et al., "Cellular immunologic responses to cochlear implantation in the human", Hearing Research vol. 318 (2014) pp. 11-17.

Clark, Graeme et al., "Biomedical studies on temporal bones of the first multi-channel cochlear implant patient at the University of Melbourne", Cochlear Implants International (2014) vol. 0 No. 0, 15 pages.

Brummer S. B. et al., "Electrical Stimulation with Pt Electrodes: Trace Analysis for Dissolved Platinum and Other Dissolved Electrochemical Products", Brain Behav. Evol. vol. 14: pp. 10-22 (1977).

Robblee, L. S. et al., "Electrical stimulation with Pt electrodes V: The effect of protein on Pt dissolution", Biomaterials vol. 1, Jan. 7, 1980, pp. 135-139.

Robblee, L. S. et al., "Electrical stimulation with Pt electrodes VII: Dissolution of Pt electrodes during electrical stimulation of the cat cerebral cortex", Journal of Neuroscience Methods, vol. 9, Mar. 11, 1983, pp. 301-308.

Razan, Abdul, "A Dielectric Study on Human Blood and Plasma", ISSN 2278-3687 (O), International Journal of Science, Environment and Technology, vol. 2, No. 6, Nov. 13, 2013, pp. 1396-1400.

Wilks, Seth et al., "Poly(3,4-ethylenedioxythiophene) as a microneural interface material for electrostimulation", doi:10.3389/neuro.16.007.2009, Jun. 9, 2009, 8 pages.

Green Rylie et al., "Conducting polymer-hydrogels for medical electrode applications", Science and Technology of Advanced Materials, vol. 11, No. 1, Mar. 18, 2010, 14 pages.

International Search Report and Written Opinion in counterpart International Application No. PCT/IB2020/055450, mailed Sep. 16, 2020, 11 pages.

Wang, C. et al., "A Selectively Permeable Membrane for Enhancing Cyclability of Organic Sodium-Ion Batteries", Advanced Materials, Aug. 29, 2016, vol. 28, Issue 41, pp. 9182-9187.

* cited by examiner

TISSUE-STIMULATING PROSTHESIS DISSOLUTION BARRIER

BACKGROUND

Field of the Invention

Certain aspects presented herein generally relate to a dissolution barrier for tissue-stimulating prostheses.

Related Art

There are several types of medical devices/implants that operate by delivering electrical (current) stimulation to the nerves, muscle, tissue fibers, or other cells of a recipient. These medical devices, sometimes referred to herein as tissue-stimulating prostheses, typically deliver current stimulation to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect, a tissue-stimulating prosthesis is provided. The tissue-stimulating prosthesis comprises: a stimulating assembly comprising an elongate carrier member and a plurality of spaced electrode contacts disposed along the elongate carrier member configured to at least one of source or sink current signals; and a dissolution barrier encapsulating the stimulating assembly, wherein the continuous dissolution barrier is configured to inhibit in situ dissolution of the plurality of electrode contacts.

In another aspect, an apparatus is provided. The apparatus comprises: an implantable carrier member formed from an insulating material and having a center longitudinal axis and an outer surface; a plurality of electrode contacts distributed on the outer surface of the carrier member along the longitudinal axis for applying electrical stimulation signals to adjacent neural tissue; and a continuous dissolution barrier layered on each of the plurality of electrode contacts and the carrier member.

In another aspect, a method is provided. The method comprises: providing a plurality of electrode contacts arranged in an elongate array; encapsulating the plurality of electrode contacts in an implantable carrier member formed from an insulating material, wherein the plurality of electrode contacts extend along a longitudinal axis of the carrier member and are positioned at an outer surface of the carrier member; exposing a surface of the each of the plurality of electrode contacts for use in applying electrical stimulation signals to adjacent neural tissue; and layering a continuous dissolution barrier on each of the plurality of electrode contacts and the carrier member.

BRIEF DESCRIPTION OF THE DRAWINGS

Embodiments of the present invention are described herein in conjunction with the accompanying drawings, in which.

DETAILED DESCRIPTION

Presented herein are dissolution barriers for use with tissue-stimulating prostheses. As described further below, a tissue-stimulating prosthesis comprises a stimulating assembly including an elongate insulating carrier member and a plurality of electrode contacts disposed along the carrier member. A continuous dissolution barrier is disposed on the surface of the stimulating assembly so as to encapsulate/enclose (e.g., substantially cover with potentially small imperfections) the plurality of electrode contacts and the carrier member. The continuous dissolution barrier is configured to inhibit in situ dissolution of the plurality of electrode contacts.

As noted, there are several types of tissue-stimulating prostheses that deliver stimulation signals (current signals) to compensate for a deficiency in a recipient. Merely for ease of illustration, the embodiments presented herein are primarily described herein with reference to one type of tissue-stimulating prosthesis, namely a cochlear implant. However, it is to be appreciated that the techniques presented herein may be used with other tissue-stimulating prostheses including, for example, auditory brainstem stimulators, implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.

Figure 1A:
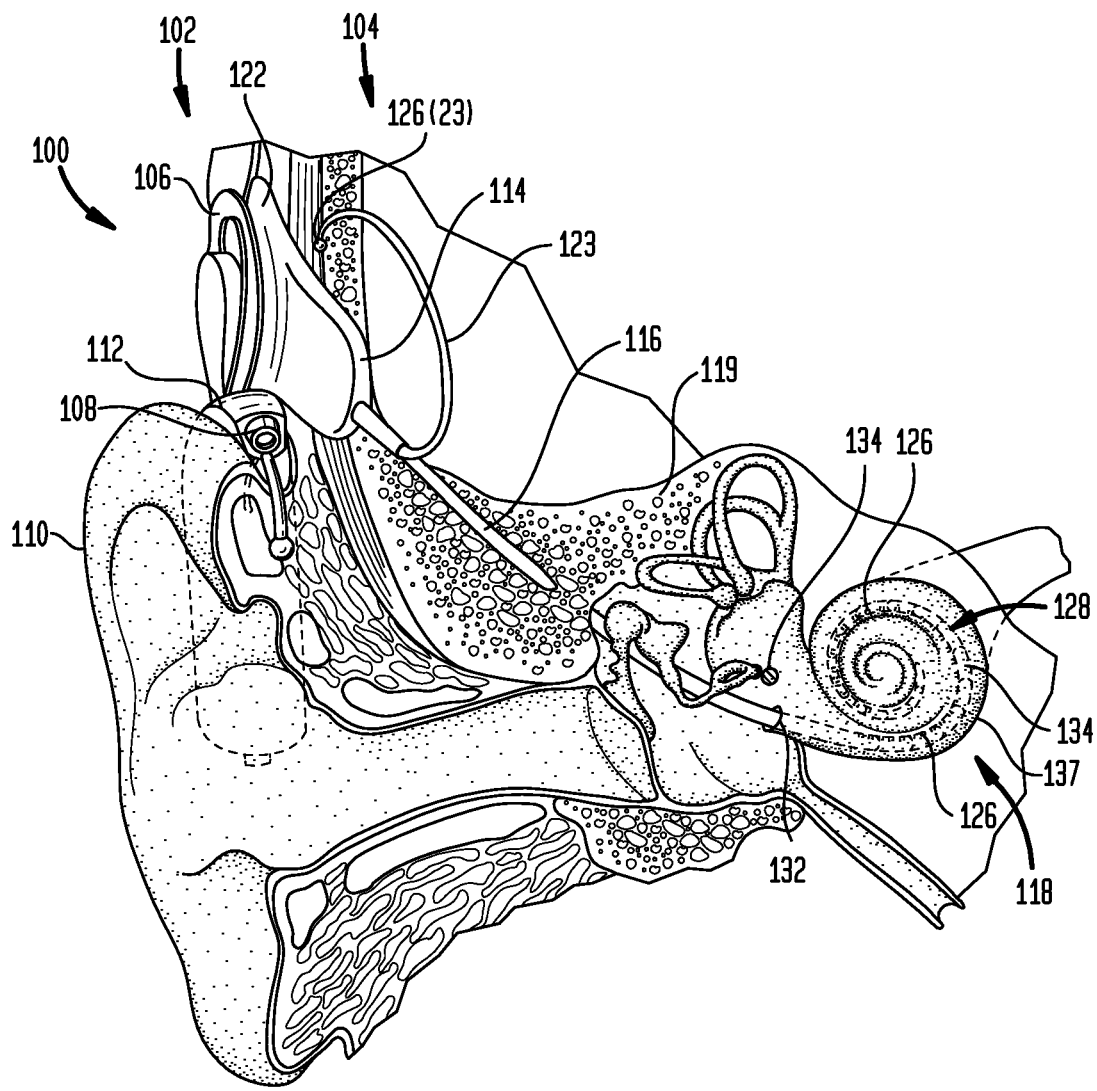
FIG. 1A is a schematic diagram illustrating a cochlear implant, in accordance with certain embodiments presented herein.
Figure 1B:
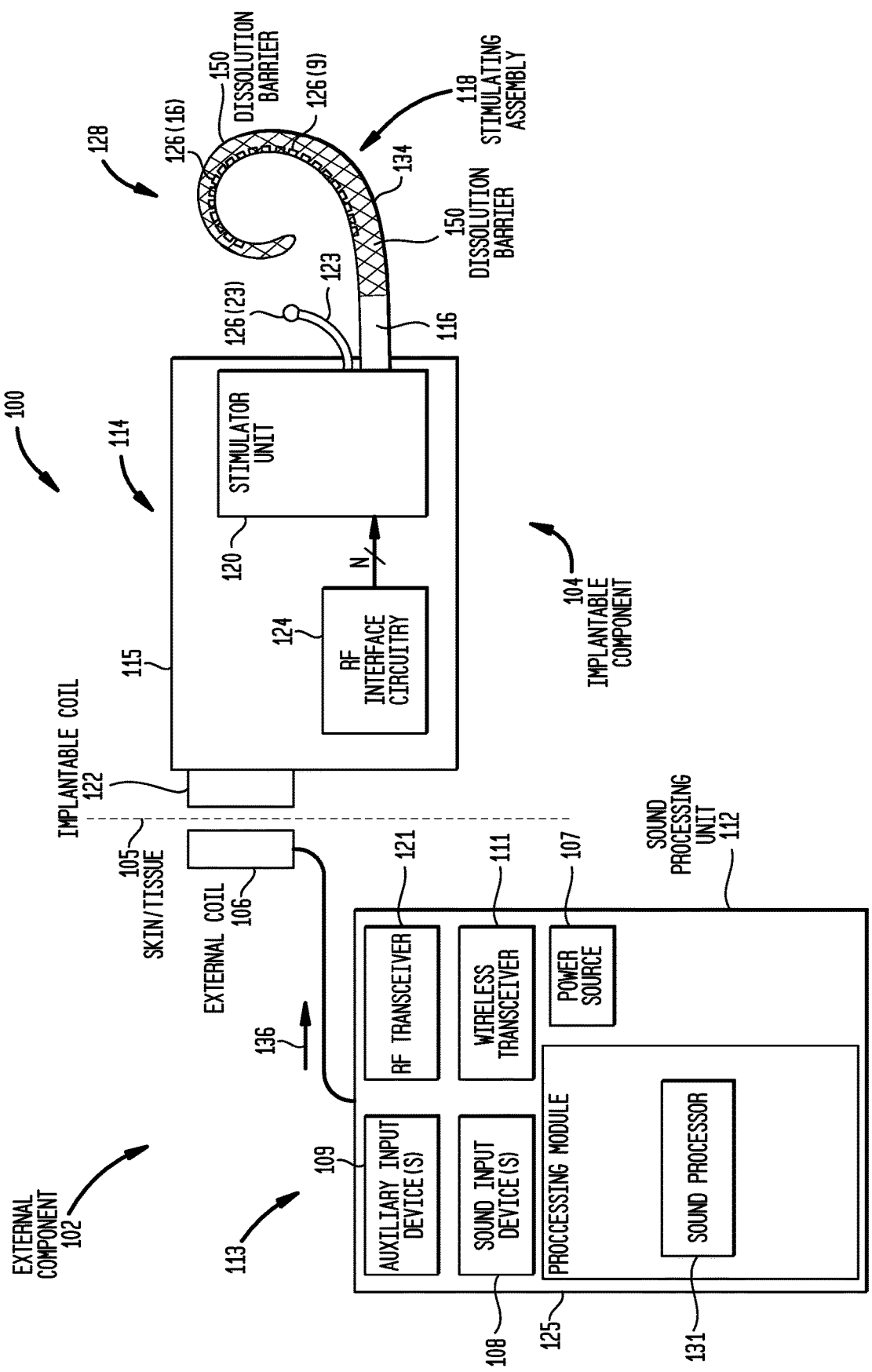
FIG. 1B is a block diagram of the cochlear implant of FIG. 1A.

FIG. 1A is a schematic diagram of an exemplary cochlear implant 100 in accordance with aspects presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input signals at a sound processing unit 112. In this example, the one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing module 125. The processing module 125 may comprise a number of elements, including a sound processor 131.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by an off-the-ear (OTE) sound processing unit (i.e., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The stimulator unit 120 comprises, among other elements, one or more current sources on an integrated circuit (IC).

The implant body 114 also includes an internal/implantable coil 122 that is generally external to the housing 115, but which is connected to the RF interface circuitry 124 via a hermetic feedthrough (not shown in FIG. 1B).

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert input audio signals into stimulation control signals 136 for use in stimulating a first ear of a recipient (i.e., the processing module 125 is configured to perform sound processing on input audio signals received at the sound processing unit 112). Stated differently, the sound processor 131 (e.g., one or more processing elements implementing firmware, software, etc.) is configured to convert the captured input audio signals into stimulation control signals 136 that represent stimulation signals for delivery to the recipient. The input audio signals that are processed and converted into stimulation control signals may be audio signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate stimulation signals (e.g., current signals) for delivery to the recipient's cochlea via the stimulating assembly 118. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

More specifically, as noted above, stimulating assembly 118 is configured to be at least partially implanted in the recipient's cochlea 137. Stimulating assembly 118 includes a plurality of longitudinally spaced intra-cochlear electrical contacts (electrode contacts or electrodes) 126 that collectively form an electrode contact array 128 configured to, for example, deliver electrical stimulation signals (current signals) generated based on the stimulation control signals 136 to the recipient's cochlea. In certain examples, the electrode contacts 126 may also be used to sink stimulation signals from the recipient's cochlea.

FIG. 1A illustrates a specific arrangement in which stimulating assembly 118 comprises twenty-two (22) intra-cochlear electrode contacts 126, labeled as electrode contacts 126(1) through 126(22). It is to be appreciated that embodiments presented herein may be implemented in alternative arrangements having different numbers of intra-cochlear electrode contacts.

As shown, the intra-cochlear electrode contacts 126(1)-126(22) are disposed in an elongate carrier member 134. The carrier member 134 has a center longitudinal axis and an outer surface. The carrier member 134 is formed from a non-conductive (insulating) material, such as silicone or other elastomer polymer. As such, the carrier member 134 electrically isolates the intra-cochlear electrode contacts 126(1)-126(22) from one another. As shown in FIG. 1B, the intra-cochlear electrode contacts 126(1)-126(22) are each spaced from one another by sections/segments of the carrier member 134.

The stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Carrier member 134 and lead region 116 each includes a plurality of conductors (wires) extending there through that electrically connect the electrode contacts 126 to the stimulator unit 120.

Also shown in FIG. 1A is an extra-cochlear electrode contact 126(23). The extra-cochlear electrode contact 126 (23) is an electrical contact that is configured to, for example, deliver electrical stimulation to the recipient's cochlea and/or to sink current from the recipient's cochlea. The extra-cochlear electrode contact 126(23) is connected to a reference lead 123 that includes one or more conductors that electrically couple the extra-cochlear electrode contact 126(23) to the stimulator unit 120.

In general, the electrode contacts of commercial cochlear implants and many other types of tissue-stimulating prostheses are formed from biocompatible and stable metallic materials (e.g., metals or metal alloys) such as, for example, a platinum group metal (e.g., platinum, osmium, iridium, ruthenium, rhodium and palladium), platinum alloyed with a small percentage of iridium, alloys of stainless steel, titanium, gold etc. Although very stable, these metallic materials do have finite dissolution rates, especially under conditions of high charge stimulation. The ex vivo analysis of long term implanted cochlear implants has revealed that some electrode contacts show signs of dissolution occurring over extended periods of time (e.g., decades).

In general, an electrode contact, which is formed from a metallic material, is comprised of atoms, from which electrons were detached and move freely in the solid. As used herein, "dissolution" of an electrode contact refers to the process of corrosion in which the metal loses electrons so as to form metal ions ($Me^{\nu+}$) that can move out of the solid (i.e., the metal ions detach from the surface). Such metallic dissolution is a kinetic process and is quantified by its rate. In tissue-stimulating prostheses, the metallic dissolution is induced by the fact that the electrode contacts are usually surrounded by, or in contact with, bodily fluid that enables the loss of the electrons and the detachment of the metal ions. The process is generally accelerated in a stimulating prosthesis because the potential of the metal changes during the delivery of a stimulating pulse. This can accelerate the dissolution process for two reasons: i) metal dissolution is generally favored thermodynamically at higher metal potentials and ii) the changing potential causes rearrangement of surface metal atoms (for example due to oxide formation and reduction), making metal atoms more likely to ionize and move away from the metal surface. The result of the removal of the metal ions is a decrease in the mass of the electrode contact (i.e., the electrode contacts corrodes).

It is expected that, if dissolution progresses indefinitely, the dissolution can affect the integrity of the electrode contacts (e.g., ultimately most of the material can be removed from the electrode contact, causing the contact to become higher impedance and eventually to stop conducting current). As a result, dissolution may limit the useful life of cochlear implants and other tissue-stimulating prostheses for at least a subset of the implanted population. Dissolution may also impact future technologies such as thin film electrodes and multipolar stimulation.

Presented herein are techniques for improving the long-term efficacy of tissue-stimulating prostheses through minimization of the dissolution rate of the tissue stimulator electrode contacts. More specifically, in accordance with embodiments presented herein, a continuous dissolution barrier encloses/encapsulates the stimulating assembly, including the electrode contacts and the s carrier member. The dissolution barrier is formed from a material that permits the conduction of electrical current, which predominantly flows in tissue by the movement of small ions such as chlorine (e.g., $Cl^-$) and sodium (e.g., $Na^+$), but inhibits the movement of metal ions from the surface of the electrode contacts. There are a number of properties that distinguish electrode metal ions from those of the predominant carrier ions in tissue. For example, electrode metals ions are generally heavier (e.g., the atomic mass of platinum is 195, whereas the atomic mass of chlorine is 35 and the atomic mass of sodium is 23). Additionally, electrode metal ions are often multivalent (e.g., platinum has two stable ionic forms ($Pt^{2+}$ and $Pt^{4+}$), whereas sodium and chlorine ions in solution are monovalent ($Cl^+$, $Na^-$). Also, heavy metal ions such as platinum typically become chelated (i.e., form stable complexes) with organic molecules such as proteins, peptides and amino acids, whereas sodium and chlorine ions exist freely in abundance in the tissue environment. All these physical differences between the electrode metal ions and majority carrier ions in tissue can be used to selectively block or reduce the movement of electrode metal ions while still allowing movement of carrier ions. Other possible barrier material types rely on non-ionic movement of charge to inhibit movement of electrode metal ions. For example, the movement of charge through conducting polymers occurs through movement of so called "polarons" which exchange charge with ions at the surface of the material. Ions themselves cannot move directly through a conductive polymer so this material is effective at blocking the movement of all ions from the metal surface, while allowing the conduction of charge through itself. Other material types, such as for example carbon nanotubes, graphene and conductive diamond also conduct charge through nonionic means can therefore be used to conduct current and simultaneously inhibit electrode metal dissolution.

In FIG. 1B, the continuous dissolution barrier is generally illustrated by reference number 150. As noted, the dissolution barrier 150 reduces electrode contact dissolution, thereby prolonging the working life of the cochlear implant 100 in situ. Further details regarding continuous dissolution barriers, such as barrier 150, are provided below.

Figure 2A:
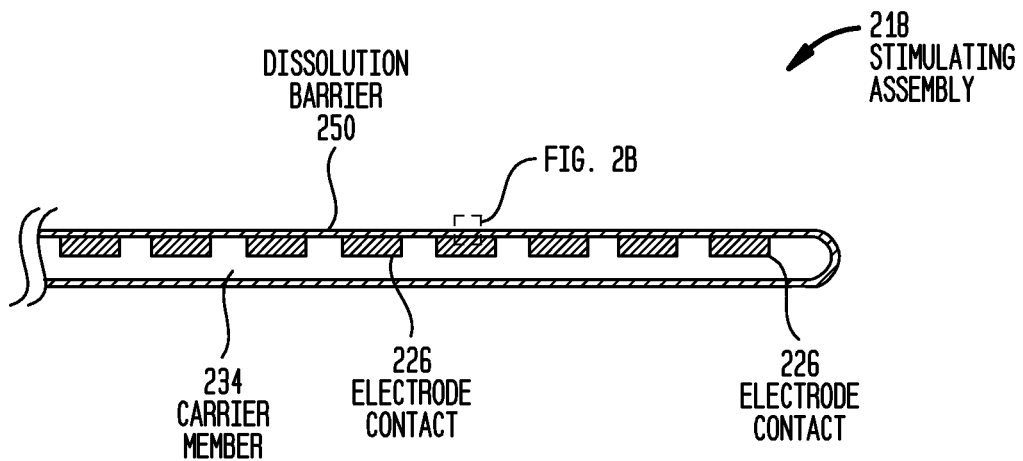
FIG. 2A is a schematic cross-sectional view of a dissolution barrier applied to a stimulating assembly, in accordance with certain embodiments presented herein.

In particular, FIG. 2A is a cross-sectional view of a continuous dissolution barrier 250 in accordance with certain embodiments presented herein. The continuous dissolution barrier 250 encapsulates stimulating assembly 218, which comprises an elongate insulating carrier member 234 and a plurality of spaced electrode contacts 226 disposed along a length of the carrier member. FIG. 2A illustrates a side view of the carrier member 234 and the plurality of electrode contacts 226 while, for ease of illustration, the dissolution barrier 250 is shown in cross-section. In practice, the dissolution barrier 250 is disposed on substantially the entire surface of the stimulating assembly 218 (i.e., the dissolution barrier 250 substantial encapsulated the entirely of the carrier member 234 and the electronic contacts 226).

Figure 2B:
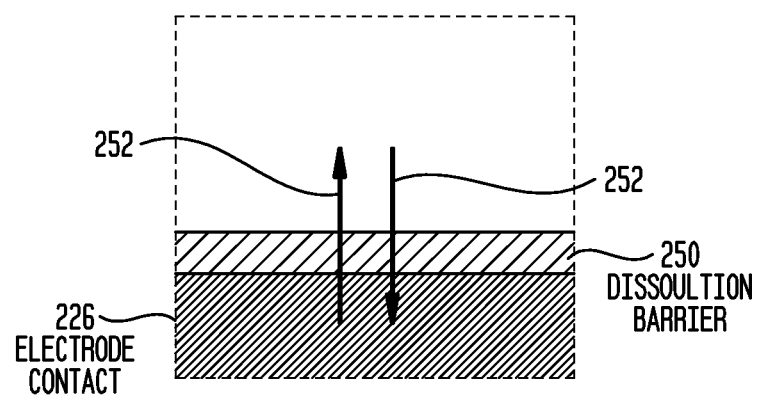
FIG. 2B is an enlarged view of a portion of the dissolution barrier of FIG. 2A disposed on an electrode contact.

FIG. 2B is an enlarged view of a portion of FIG. 2A, illustrating a section of the dissolution barrier 250 and an electrode contact 226. As shown by arrows 252, the dissolution barrier 250 is configured such that electrical current flows across/thru the dissolution barrier 250. However, the dissolution barrier 250 is also configured such that the dissolution barrier 250 blocks metal (e.g., platinum) atoms and ions, as described above. That is, the platinum atoms and ions remain trapped behind (under) the dissolution barrier 250 (i.e., the platinum atoms and ions remain at the electrode contacts 226).

In accordance with embodiments presented herein, the dissolution barrier 250 may be a continuous coating, sheath, jacket, film, layer, membrane, or other type of barrier applied to the carrier member 234 and electrode contacts 226. The dissolution barrier 250 is configured to inhibit the rate of removal of metal (e.g., platinum) ions from the electrode contact surface and has sufficiently high conductivity to allow the passage of electrical current across/through it without adding excessive impedance to the neural stimulating path (i.e., without adding excessive impedance to the current signals sourced or sunk via the electrode contacts). However, the dissolution barrier 250 is configured such that it has sufficiently low conductivity to inhibit significant shunting of electrical current between electrode contacts.

Therefore, as described further below, dissolution barriers in accordance with embodiments presented herein, such as dissolution barrier 250, have a conductivity that is below an upper limit/threshold, but a conductivity that is above a lower limit/threshold. If the conductivity of a dissolution barrier is too high, then the dissolution barrier will shunt too much current between electrode contacts (e.g., in contrast to a layer positioned only on electrode contacts which would have no upper conductivity limit).

Moreover, if the conductivity of the dissolution barrier is too low, then the dissolution barrier will significantly increase the impedance of the electrode, consuming more power and limiting current flow to the target nerve (e.g., auditory nerve). Therefore, a conductivity that is too high or too low can make the tissue-stimulating prosthesis unusable for the intended purpose and/or negatively affect the performance of the tissue-stimulating prosthesis. The appropriate conductivity range for a dissolution barrier is discussed below and depends on the thickness of the barrier material and the size of the electrode contacts.

It is to be noted that reducing the thickness of the barrier material may be advantageous in both reducing the added impedance and in reducing the shunt current flowing therein. Therefore, in general, the barrier material should be made as thin as possible. However, the constraints of the application process, such as the thickness of a dip coated layer or the fragility of an applied film, may dictate a minimum thickness for the barrier material. Once this minimum thickness (as determined based on the application process) is established, the conductivity of the applied barrier material can be adjusted to ensure the added impedance and shunt current are both within tolerable limits. The conductivity of candidate barrier materials can usually be adjusted by adjusting the chemistry of the manufacturing process. For example, the conductivity of conducting polymers can be adjusted by a method known as organic synthesis, where different organic molecules are incorporated into the molecular structure of the polymer, affecting its conductivity. Generally even very thin layers of barrier material are sufficient to block the flow of electrode metal ions. So the efficiency of the barrier material in blocking metal electrode ions is rarely a factor when determining the thickness of the barrier material.

Figure 3A:
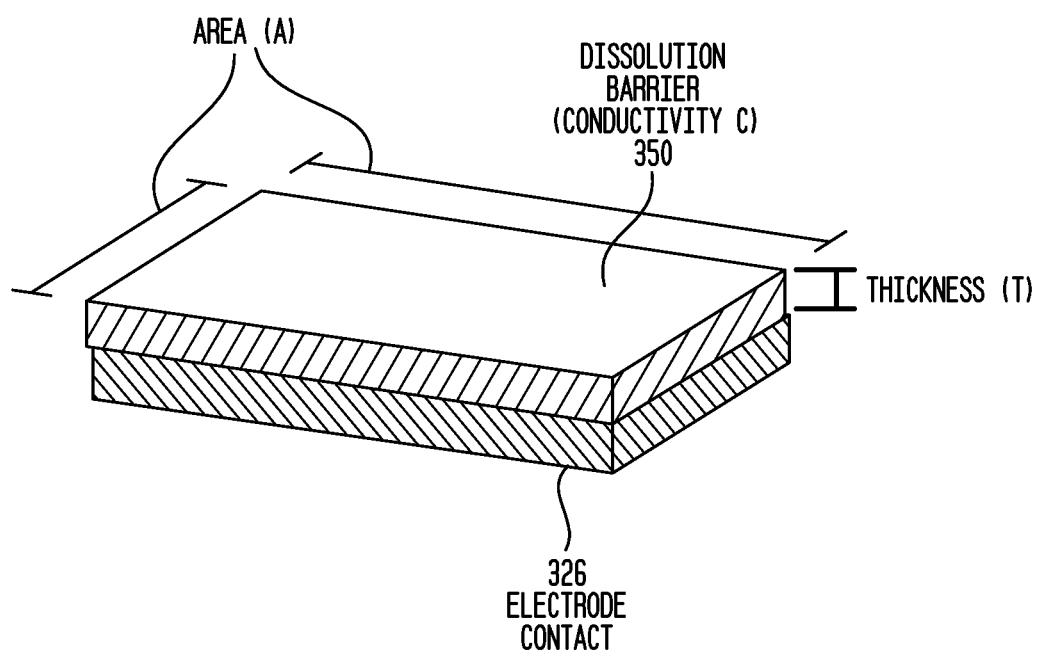
FIG. 3A is a schematic diagram illustrating variables used to calculation different parameters for a dissolution barrier, in accordance with certain embodiments presented herein.

FIG. 3A generally illustrate the variables used in calculations of different parameters for a dissolution barrier in accordance with embodiments presented herein. More specifically, shown in FIG. 3A is an electrode contact 366 with a surface area, A, and a portion of a dissolution barrier 350 made from a material with a conductivity, C, and a thickness, T, where the conductivity is given in Siemens per meter ($Sm^{-1}$). The impedance, Z, of the dissolution barrier 350 is then given as shown below in Equation 1.

$$Z = T/(A \cdot C) \qquad \text{Equation 1:}$$

As shown below in Equation 2, Equation 1 can be arranged to solve for C.

$$C = T/(A \cdot Z) \qquad \text{Equation 2:}$$

If the impedance, Z, has a maximum acceptable value, $Z_{max}$, then the equation for the minimum conductivity, $C_{min}$, is shown below in Equation 3.

$$C_{min} = T/(A \cdot Z_{max}) \qquad \text{Equation 3:}$$

In one example, it is assumed that the electrode contacts 326 each have surface area of 0.15 $mm^2$ (i.e., A equals 0.15 $mm^2$, which is typical for certain cochlear implant electrode contacts). It is also assumed that the dissolution barrier 350 has a thickness of 0.1 mm and is made from a material of conductivity, C $Sm^{-1}$ (i.e., T equals 0.1 mm and C is an unknown variable). It is also assumed that the acceptable maximum impedance for the dissolution barrier 350 is 1 Kiloohm (kΩ) (i.e., $Z_{max}$ equals 1 kΩ). In this example, the example acceptable maximum impedance is based on the total impedance of an electrode contact of the above dimensions in a typical cochlea. In particular, 1 kΩ is approximately 10% of the total impedance of an electrode of those dimensions in a typical cochlea.

If the above values of A=0.15 $mm^2$, T=0.1 mm, and $Z_{max}$ 1 kΩ are used in Equation 3, the minimum value of C (i.e., $C_{min}$) is approximately 0.67 $Sm^{-1}$ (i.e., $10^{-4}/(1.5 10^{-7} \cdot 10^3)$). This is the minimum acceptable value of conductivity, C, for dissolution barrier 350 since any higher value would result in an impedance for the dissolution barrier being greater than 1 kΩ. If the value of acceptable maximum impedance would change, the minimum acceptable value of conductivity would also change. It is to be noted that all units in the above equations are expressed in SI units.

As noted above, in cochlear implants, the stimulating assembly is implanted within one of the recipient's cochlea ducts/canals, namely within the scala vestibuli or the scala tympani. Each of the scala vestibuli and the scala tympani are filled with a conductive fluid known as perilymph. The perilymph of the scala vestibuli, and that of the scala tympani have compositions similar to cerebro-spinal fluid (CSF), namely rich in sodium (140 mM) and poor in potassium (5 mM) and calcium (1.2 mM). The perilymph in the scala vestibuli comes from blood plasma across a hemto-perilymphatic barrier, whereas that of the scala tympani originates from CSF. The perilymph is conductive to electrical current.

As noted, in above example the minimum conductivity for the dissolution barrier is approximately 0.67 $Sm^{-1}$. Now, it is assumed that the maximum acceptable conductivity for the barrier material is the same as the conductivity of perilymph, namely approximately 180 $Sm^{-1}$, which is similar to that blood plasma. If the conductivity is any higher than that of perilymph, then this would increase the flow of current between the electrode contacts during stimulation.

Figure 3B:
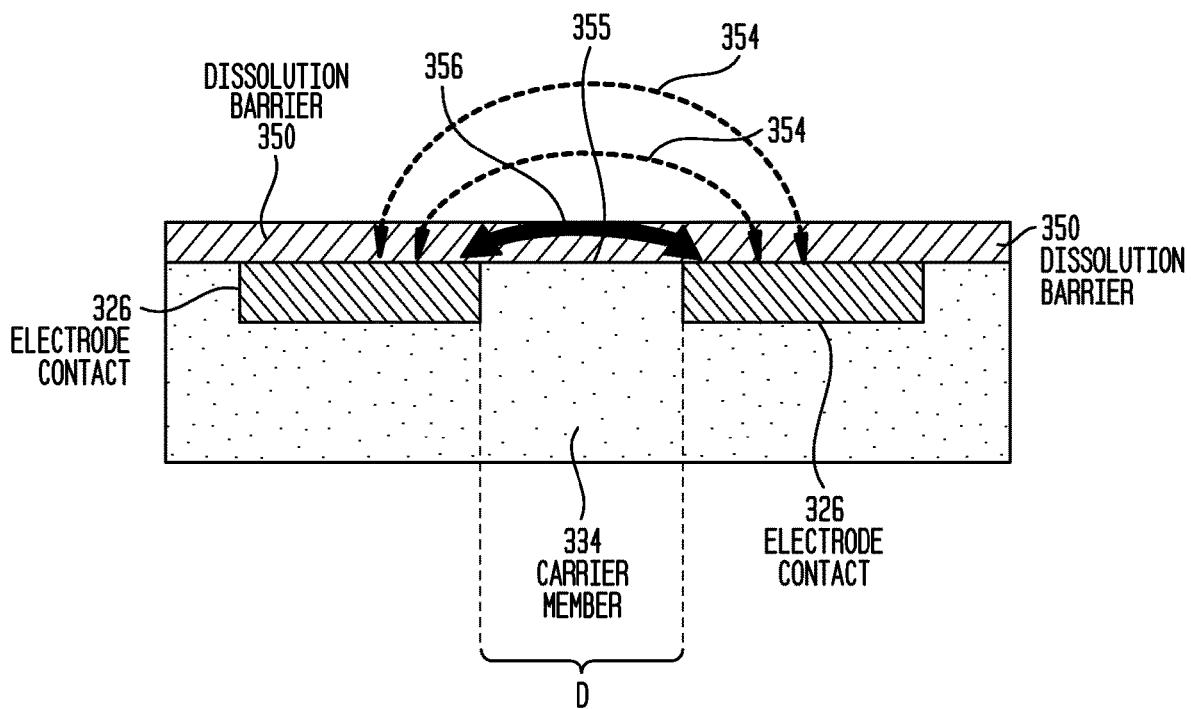
FIG. 3B is a schematic diagram illustrating the shunting of current between electrode contacts for a barrier material with improper conductivity.

FIG. 3B is a schematic diagram illustrating the shunting of current between electrode contacts if the conductivity of the dissolution barrier 350 is set too high. In FIG. 3B, two electrode contacts 326 are disposed in an insulating carrier member 334 (e.g., formed from silicone) and separated by a section/portion 355 of the carrier member 334 having a length of D (i.e., the electrode contacts are separated/spaced from another by a distance, D). As shown by arrows 354, a conductivity for the dissolution barrier 350 that is too high minimizes the normal current paths into the recipient's tissue. As shown by arrow 356, minimization of the normal current results in excessive current flow between the electrode contacts 326 through/via the dissolution barrier 350.

It is noted that the conductivity of perilymph is fairly high and causes significant power loss in convention cochlear implants. Choosing an upper conductivity limit to be the same as that of perilymph means that the dissolution barrier will not make the electrical situation worse (i.e., no additional current will be shunted between electrodes contacts by the presence of the dissolution barrier). In certain embodiments, the dissolution barrier may have a conductivity that is less than that of the perilymph or other surrounding body tissue/fluid. For example, the dissolution barrier may have a conductivity that is approximately 5% or 10% less than that of the conductivity of the perilymph. However, in certain embodiments, it may be acceptable to use a dissolution barrier that has somewhat higher conductivity than that of perilymph if the trade-off (e.g. better dissolution prevention) is sufficiently high. The practical disadvantages of using a higher conductivity material are likely to be higher power consumption and possibly increase spread of excitation of the auditory nerve.

In the above example, the acceptable range of conductivity for a dissolution barrier of approximately 0.1 mm thickness, T, and an electrode area, A, of 0.15 mm$^2$ is between approximately 0.67 Sm$^{-1}$ and approximately 180 Sm$^{-1}$ (0.67<C<180 Sm$^{-1}$). It would be appreciated that for other barrier thicknesses the range will be different. Assuming once again a maximum additional impedance of 1 kΩ and an electrode area 1.5·10$^{-7}$ m$^2$ (0.15 mm$^2$), then, as shown below in Equation 4, Equation 3 can be written in terms of the barrier material thickness, T, to find the minimum acceptable conductivity, $C_{min}$.

$$C_{min} = T/1.5 \cdot 10^{-4} \qquad \text{Equation 4:}$$

As such, for a thickness, T, equal to 0.05 mm, the minimum conductivity, $C_{min}$, is then 5·10$^{-5}$/1.5·10$^{-4}$, or 0.33 Sm$^{-1}$. Hence for a 0.05 mm thick dissolution barrier, the range of conductivity, C, is between approximately 0.33 Sm$^{-1}$ and approximately 180 Sm$^{-1}$ (0.33<C<180 Sm$^{-1}$).

As detailed above, a dissolution barrier in accordance with embodiments presented herein has a conductivity that is below an upper limit/threshold, but also a conductivity that is above a lower limit/threshold. If the conductivity of a dissolution barrier is too high, then the dissolution barrier will shunt too much current between electrode contacts, while if the conductivity is too low it will add impedance to the stimulating path. In other words, the dissolution barrier is sufficiently electrically conductive to not add significant impedance (e.g., more than 1 kOhm) to the electrical stimulation path, yet sufficiently electrically insulating to not shunt significant current between electrode contacts. In addition to the above, a dissolution barrier in accordance with embodiments presented herein may also have additional properties.

For example, a dissolution barrier in accordance with embodiments presented herein may be configured to be applied through a reproducible manufacturing process. Examples of reproducible manufacturing processes include, for example, dip coating, spraying, shrink wrapping, etc. Additionally, a dissolution barrier in accordance with embodiments presented herein is biocompatible, will not degrade during a sterilization process, and will remain stable in the cochlea over many decades. Moreover, a dissolution barrier in accordance with embodiments presented herein is configured such that it will not affect the mechanical characteristics of the stimulating assembly and is close to, or in contact with, the carrier member and electrode contacts (e.g., to avoid increasing the array's cross-sectional area and making it harder to insert). The dissolution barrier is generally relatively thin so as to: minimize additional stimulation impedance for a given material conductivity, minimize current shunting between adjacent electrode pads for a given material conductivity, minimize the total cross-section of the electrode array, and minimize any mechanical changes to the array caused by the mechanical characteristics of the barrier.

In specific example, a dip coating is used to apply the dissolution barrier to a stimulating assembly. For example, at the end of the stimulating assembly manufacturing process, a completed stimulating assembly (i.e., electrodes embedded in a carrier member) is dipped in a solution which contains a soluble form of the barrier material. Once the material dries or hardens it forms a solid, flexible coating on the stimulating assembly. In another example, a liquid barrier material is applied via an apparatus that sprays a mist onto the stimulating assembly. In other examples, a shrink wrapping process takes a thin, solid form of the barrier material (e.g., similar to cling film or shrink warp) and wraps it around the stimulating assembly. Once the wrapping is in place heat would be applied through a hot air gun or similar and the wrapping would shrink to a snug fit on the stimulating assembly.

A dissolution barrier in accordance with embodiments presented herein may be formed from a number of different material types that fulfil many of the above characteristics. For example, in certain embodiments, the dissolution barrier may be formed from biocompatible conducting polymers or biocompatible conducting hydrogels. In further embodiments, the dissolution barrier may be formed from dissolution resistant nanoparticles such as carbon nanotubes suspended in biocompatible polymers, plastics, silicones or other insulating solids. In further embodiments, the dissolution barrier may be formed from woven biocompatible material, such as insulating polymers or plastics. For example, it may be that finely woven mats of insulating materials can be made with sufficient porosity to allow the passage of charge carrying ions while reducing the flow of larger metal ions, such as platinum ions.

Figure 4:
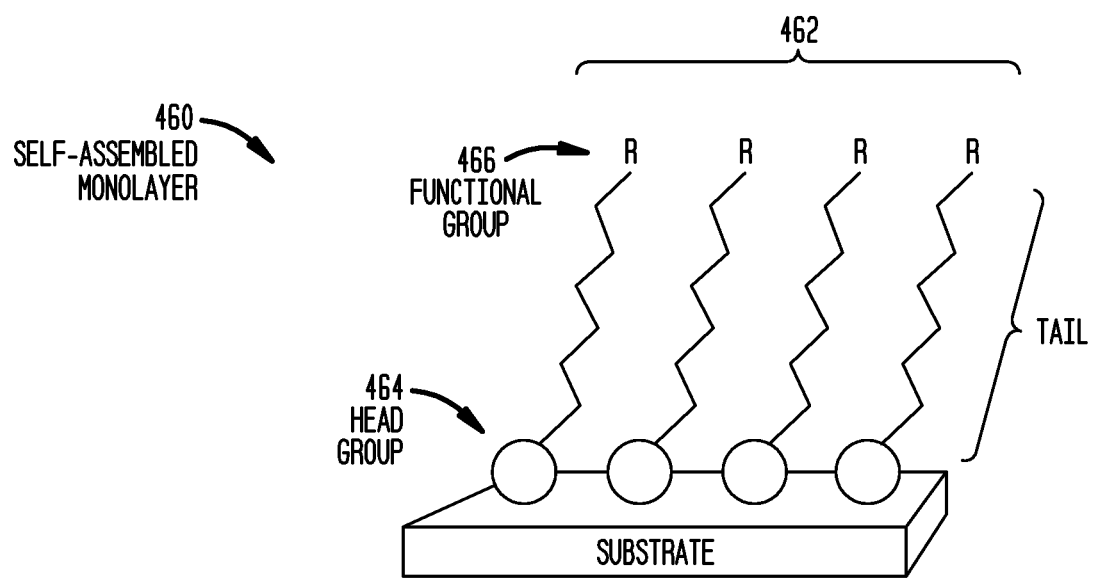
FIG. 4 is a schematic diagram illustrating a self-assembled monolayer forming a dissolution barrier, in accordance with certain embodiments presented herein.

In certain embodiments, the dissolution barrier may be formed from self-assembled monolayers. As shown in FIG. 4, a self-assembled monolayer 462 is formed from carbon chain molecules 462 with thiol or "head" groups 464 that promote adhesion to conductors and with functional groups 466, such as proteins, at the other end thereof. The thiol groups 464 can be used to firmly attach the carbon chain molecules 462 to surfaces that may not attach as easily without the self-assembled monolayer 462. If the carbon chains 462 are made short, then the self-assembled monolayer 462 can present a low impedance to the passage of current and, depending on the functional group, may also be effective in inhibiting metal ions from diffusion from the surface.

In certain examples, the dissolution barrier may be formed from ion permeable membranes. Ion permeable membranes are materials that allow the movement of conducting ions through drift, but which block the diffusion of platinum ions. This selectivity (to conducting ions through drift but not to the diffusion of platinum ions) can be based on several factors. For example, the selectivity may be based on the size of the ion, where platinum ions (e.g., [PtCl$_4$]$^{2-}$) are large, but the main current carrying ions (e.g., Cl$^-$, Na$^+$, K$^+$) are small. The selectivity may also or alternatively be based on the valency of the ions (i.e., platinum ions are divalent whereas the current carrying ions are monovalent). The selectivity may also or alternatively be based on the actual drift versus diffusion properties, where current carrying ions move under the influence of electric fields, but diffused ions do not. The selectivity may also or alternatively be based on frequency, where charge carrying ions move rapidly in a tissue-stimulating prosthesis, but platinum ions move much more slowly under the influence of diffusion and other transport mechanisms in the body.

In certain examples, the dissolution barrier may be formed from doped crystalline materials, such a nitrogen doped diamond and titanium nitride. These materials can provide low impedance interfaces and are usually applied using sputter, vapour or other deposition techniques.

Embodiments have primarily been described herein with reference to dissolution barriers principally configured to inhibit the dissolution of the electrodes, without negatively affecting the stimulation pathway and without burdening the manufacturing process. That is, dissolution barriers in accordance with embodiments presented herein are sufficiently solid to block the transport of platinum atoms, ions, or particles (i.e., substantially prevent the dissolution of the platinum electrode contacts in the presence of bodily fluid), yet have a conductivity that is above a lower limit/threshold, but still below an upper limit/threshold (i.e., a proper conductivity to allow the stimulation current to pass through the barrier without significant increases in impedance, yet without shorting adjacent electrode contacts to one another). In addition to the above, a dissolution barrier in accordance with embodiments presented herein may also have additional properties that serve other functions.

For example, a dissolution barrier in accordance with embodiments presented may, in addition to the above platinum blocking and conductivity limits, be configured for drug elution, lubrication, etc.

As noted above, the electrode contacts are used to deliver stimulation signals (current) to tissue of the recipient. In certain prostheses, the electrode contacts are each solid conductive elements of a certain thickness (e.g., cut or punched from a sheet or tube of platinum, platinum alloy, etc.). More recently, attempts have been made to use microfabrication techniques, such as photolithography, thin film deposition, etc. to fabricate the electrode contacts on, for example, silicon substrates. Thin film deposition, for example, is a process in which a very thin film of material (e.g., a few nanometers to about 100 micrometers) is applied onto a "substrate" surface, or onto a previously deposited coating. Therefore, a "thin-film" or "micro" electrode contact is comprised of several layers of thin conductive material layered on top of one another on an insulating substrate.

The final thickness of a thin-film electrode can vary depending, for example, on the use, manufacturing process, etc. However, thin-film electrodes are generally much thinner than conventional electrode contacts and, as a result, are susceptible to long term issues arising from dissolution. That is, since thin-film electrodes have less thickness than conventional electrodes, thin-film electrodes can afford to lose less material before becoming ineffective. Therefore, dissolution barriers in accordance with embodiments presented herein may be particularly advantageous within thin-film electrodes.

In one example, a preformed solid film of barrier material may be applied to a thin film electrode as the film only needs to coat one side of the essentially two sided electrode. A separate film of barrier material can be stretched over the electrode and trimmed away. It may be possible to apply a thin layer of adhesive to the film to keep it in place and/or electrostatic forces may be used to retain the film in place (e.g., as with cling film or shrink warp). In certain embodiments, the barrier material could be added as an additional step in the thin film processing.

Figure 5:
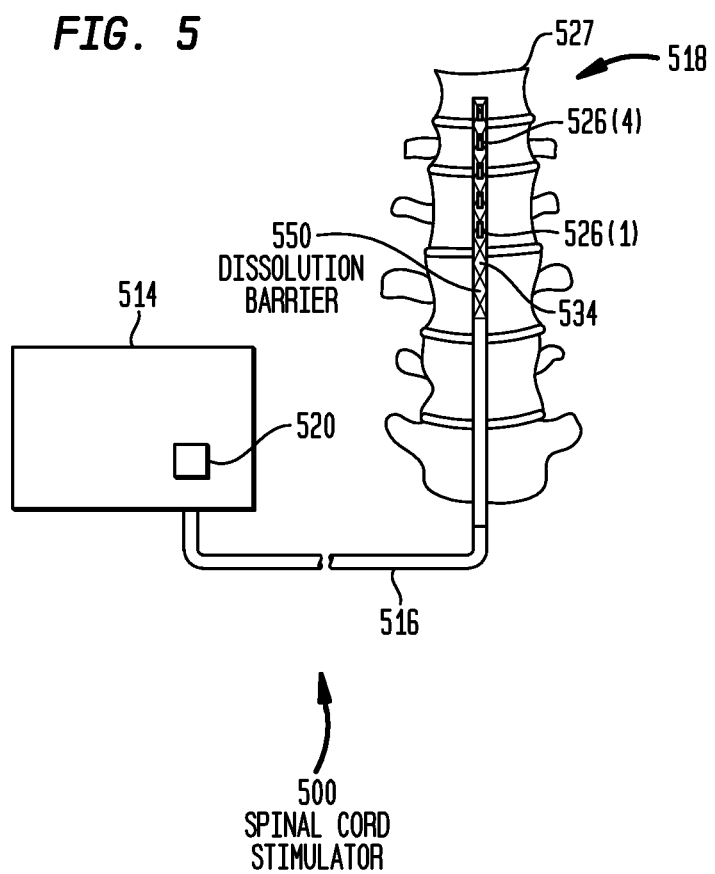
FIG. 5 is a schematic diagram of a spinal cord stimulator, in accordance with certain embodiments presented herein.

Embodiments presented herein have primarily been described with reference to cochlear implants. However, as noted elsewhere wherein, the techniques presented herein may also or alternatively be used with other types of tissue stimulating prostheses (e.g., auditory brainstem stimulators, implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.). FIG. 5 is a simplified schematic diagram illustrating an example spinal cord stimulator 500 in which embodiments presented herein may be implemented.

The spinal cord stimulator 500 comprises an implant body (main module) 514, a lead region 516, and a stimulating assembly 518. The implant body 514 includes a stimulator unit 520 comprising, among other elements, one or more current sources on an integrated circuit (IC).

The stimulating assembly 518 is implanted in a recipient adjacent/proximate to the recipient's spinal cord 527 and comprises five (5) stimulation electrodes 526, referred to as stimulation electrodes 526(1)-526(5). The stimulation electrodes 526(1)-526(5) are disposed in an electrically-insulating carrier member 534 and are electrically connected to the stimulator 520 via conductors (not shown) that extend through the carrier member 534.

Following implantation, the stimulator unit 520 generate stimulation signals for delivery to the spinal cord 527 via stimulation electrodes 526(1)-526(5). Although not shown in FIG. 5, an external controller may also be provided to transmit signals through the recipient's skin/tissue to the stimulation electronics 633 for control of the stimulation signals.

Similar to the embodiments described above, the stimulating assembly 518 comprises a dissolution barrier 550 configured to reduce electrode contact dissolution, thereby prolonging the working life of the spinal cord stimulator 500 in situ. The dissolution barrier 550 is configured such that electrical current flows across/thru the dissolution barrier 550, but is also configured such that the dissolution barrier 550 blocks platinum atoms and ions. That is, the platinum atoms and ions remain trapped behind (under) the dissolution barrier 5250 (i.e., the platinum atoms and ions remain at the electrode contacts 526).

In accordance with embodiments presented herein, the dissolution barrier 550 may be a continuous coating, sheath, jacket, film, layer, membrane, or other type of barrier applied to the carrier member 534 and electrode contacts 526. The dissolution barrier 550 is configured to reduce the rate of removal of platinum ions from the electrode contact surface and has sufficiently high conductivity to allow the passage of electrical current across/through it without adding excessive impedance to the neural stimulating path. However, the dissolution barrier 550 is configured such that it has sufficiently low conductivity to prevent significant shunting of electrical current between electrode contacts.

Figure 6:
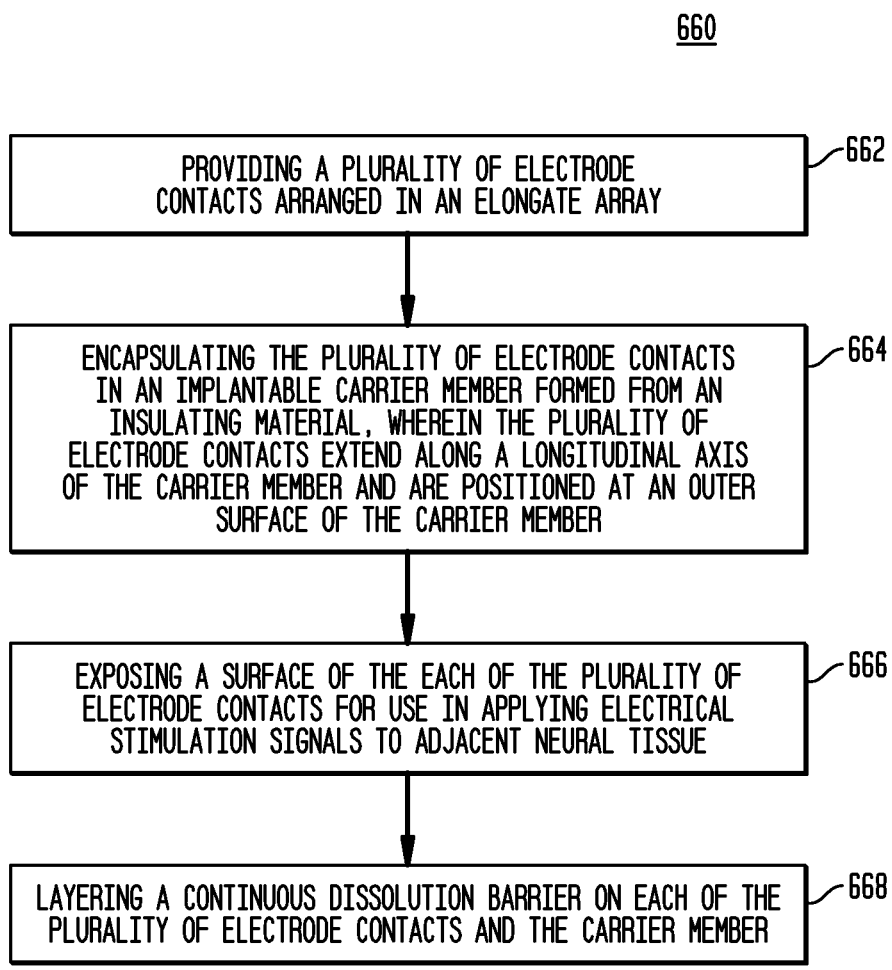
FIG. 6 is a flowchart of a method, in accordance with certain embodiments presented herein.

FIG. 6 is a flowchart of a method 660 in accordance with certain embodiments presented herein. Method 660 begins at 662 where a plurality of electrode contacts arranged in an elongate array are provided. At 664, the plurality of electrode contacts are encapsulated in an implantable carrier member formed from an insulating material. The plurality of electrode contacts extend along a longitudinal axis of the carrier member and are positioned at an outer surface of the carrier member. At 666, a surface of the each of the plurality of electrode contacts is exposed for use in applying electrical stimulation signals to adjacent neural tissue. At 668, a continuous dissolution barrier is layered on each of the plurality of electrode contacts and the carrier member.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A tissue-stimulating prosthesis, comprising:
   a stimulating assembly comprising an elongate carrier member and a plurality of electrode contacts disposed along the elongate carrier member configured to at least one of source or sink current signals; and
   a dissolution barrier encapsulating the stimulating assembly, wherein the dissolution barrier is configured to inhibit movement of metal ions from a surface of the plurality of electrode contacts to inhibit in situ dissolution of the plurality of electrode contacts.

2. The tissue-stimulating prosthesis of claim 1, wherein the dissolution barrier is configured to permit conduction of electrical current.

3. The tissue-stimulating prosthesis of claim 1, wherein the dissolution barrier has a conductivity, and wherein the conductivity is greater than a first threshold and lower than a second threshold.

4. The tissue-stimulating prosthesis of claim 3, wherein the first and second thresholds are selected based on a surface area of the plurality of electrode contacts and a thickness of the dissolution barrier.

5. The tissue-stimulating prosthesis of claim 3, wherein the stimulating assembly is configured to be implanted in a recipient in a location in which the dissolution barrier is in contact with a body fluid of the recipient, and wherein the second threshold is approximately the same as a conductivity of the body fluid.

6. The tissue-stimulating prosthesis of claim 3, wherein the stimulating assembly is configured to be implanted in a recipient in a location in which the dissolution barrier is in contact with a body fluid of the recipient, and wherein the second threshold is less than a conductivity of the body fluid.

7. The tissue-stimulating prosthesis of claim 6, wherein the stimulating assembly is configured to be implanted in a recipient's cochlea such that the dissolution barrier is in contact with perilymph of the recipient, and wherein the second threshold is approximately 180 Siemens per meter ($Sm^{-1}$).

8. The tissue-stimulating prosthesis of claim 3, wherein the first threshold is a level at which an impedance of the dissolution barrier is less than 10% of a total impedance of each of the plurality of electrode contacts.

9. The tissue-stimulating prosthesis of claim 3, wherein the first threshold is approximately 1 Kiloohm ($k\Omega$).

10. The tissue-stimulating prosthesis of claim 3, wherein the first threshold is a minimum conductivity ($C_{min}$) given in Siemens per meter, and wherein:

$$C_{min}=T/1.5\cdot 10^{-4},$$

wherein T is a barrier material thickness in meters.

11. The tissue-stimulating prosthesis of claim 1, wherein the dissolution barrier comprises at least one of a biocompatible conducting polymer or a biocompatible conducting hydrogel.

12. The tissue-stimulating prosthesis of claim 1, wherein the dissolution barrier comprises dissolution resistant nanoparticles suspended in at least an insulating solid.

13. The tissue-stimulating prosthesis of claim 1, wherein the dissolution barrier comprises at least one of a biocompatible woven insulating polymer or plastic.

14. The tissue-stimulating prosthesis of claim 1, wherein the dissolution barrier comprises a self-assembled monolayer.

15. The tissue-stimulating prosthesis of claim 1, wherein the dissolution barrier comprises an ion permeable membrane configured to selectively allow movement of conducting ions through drift while blocking diffusion of the metal ions.

16. The tissue-stimulating prosthesis of claim 15, wherein the ion permeable membrane is configured to selectively allow movement of conducting ions through drift while blocking diffusion of the metal ions based on at least one of a size of the conducting ions, a valency of the conducting ions, or a frequency of movement of the conducting ions.

17. The tissue-stimulating prosthesis of claim 1, wherein the plurality of electrode contacts includes thin-film electrode contacts.

18. An apparatus, comprising:
    an implantable carrier member formed from an insulating material and having a center longitudinal axis and an outer surface;
    a plurality of electrode contacts distributed on the outer surface of the implantable carrier member along the center longitudinal axis for applying electrical stimulation signals to adjacent neural tissue; and
    a continuous dissolution barrier layered on each of the plurality of electrode contacts and the implantable carrier member, wherein the continuous dissolution barrier is configured to inhibit movement of metal ions from a surface of the plurality of electrode contacts.

19. The apparatus of claim 18, wherein electrode contacts of the plurality of electrode contacts are each spaced from one another by sections of the implantable carrier member, and wherein the continuous dissolution barrier is layered on the plurality of electrode contacts and the sections of the implantable carrier member between the plurality of electrode contacts.

20. The apparatus of claim 18, wherein the continuous dissolution barrier is configured to permit conduction of electrical current.

21. The apparatus of claim 18, wherein the continuous dissolution barrier has a conductivity, and wherein the conductivity is greater than a first threshold and lower than a second threshold.

22. The apparatus of claim 21, wherein the first and second thresholds are selected based on a surface area of the plurality of electrode contacts and a thickness of the continuous dissolution barrier.

23. The apparatus of claim 21, wherein the apparatus is configured to be at least partially implanted in a recipient in a location in which the continuous dissolution barrier is in contact with a body fluid of the recipient, and wherein the second threshold is approximately the same as a conductivity of the body fluid.

24. The apparatus of claim 21, wherein the apparatus is configured to be at least partially implanted in a recipient in a location in which the continuous dissolution barrier is in contact with a body fluid of the recipient, and wherein the second threshold is less than a conductivity of the body fluid.

25. The apparatus of claim 18, wherein the continuous dissolution barrier comprises an ion permeable membrane configured to selectively allow movement of conducting ions through drift while blocking diffusion of the metal ions.

26. The apparatus of claim 25, wherein the ion permeable membrane is configured to selectively allow movement of conducting ions through drift while blocking diffusion of the metal ions based on at least one of a size of the conducting ions, a valency of the conducting ions, or a frequency of movement of the conducting ions.

27. A method, comprising:
providing a plurality of electrode contacts arranged in an elongate array;
encapsulating the plurality of electrode contacts in an implantable carrier member formed from an insulating material, wherein the plurality of electrode contacts extends along a longitudinal axis of the implantable carrier member and is positioned at an outer surface of the implantable carrier member;
exposing a surface of each of the plurality of electrode contacts for use in applying electrical stimulation signals to adjacent neural tissue; and
layering a continuous dissolution barrier on each of the plurality of electrode contacts and the implantable carrier member, wherein the continuous dissolution barrier is configured to inhibit movement of metal ions from the surface of the plurality of electrode contacts.

28. The method of claim 27, wherein layering the continuous dissolution barrier on each of the plurality of electrode contacts and the implantable carrier member comprises:
dip coating the implantable carrier member with the plurality of electrode contacts.

29. The method of claim 27, wherein layering the continuous dissolution barrier on each of the plurality of electrode contacts and the implantable carrier member comprises:
spraying the continuous dissolution barrier onto each of the plurality of electrode contacts and the carrier member.

30. The method of claim 27, wherein the continuous dissolution barrier has a conductivity, and wherein the conductivity is greater than a first threshold and lower than a second threshold.

* * * * *